(12) United States Patent
Miller

(10) Patent No.: US 9,414,862 B2
(45) Date of Patent: Aug. 16, 2016

(54) BONE FASTENER FOR A SPINAL SURGICAL SYSTEM

(75) Inventor: Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 68 days.

(21) Appl. No.: 13/279,387

(22) Filed: Oct. 24, 2011

(65) Prior Publication Data

US 2013/0103096 A1 Apr. 25, 2013

(51) Int. Cl.
| | | |
|---|---|---|
| A61B 17/04 | (2006.01) | |
| A61B 17/86 | (2006.01) | |
| A61F 2/08 | (2006.01) | |
| A61B 17/70 | (2006.01) | |
| A61B 19/00 | (2006.01) | |

(52) U.S. Cl.
CPC ......... *A61B 17/7032* (2013.01); *A61B 17/7077* (2013.01); *A61B 17/7082* (2013.01); *A61B 17/7085* (2013.01); *A61B 17/7037* (2013.01); *A61B 2019/307* (2013.01)

(58) Field of Classification Search
CPC ............. A61B 17/8605; A61B 17/861; A61B 17/864; A61B 17/7083; A61B 17/7085
USPC ............. 606/264–278, 300–321, 96, 99, 104, 606/86 A
See application file for complete search history.

(56) References Cited

U.S. PATENT DOCUMENTS

| | | | |
|---|---|---|---|
| 5,403,316 A | 4/1995 | Ashman | |
| 5,738,685 A | 4/1998 | Halm et al. | |
| 6,540,749 B2 | 4/2003 | Schafer et al. | |
| 6,702,814 B2 | 3/2004 | Walulik et al. | |
| 7,188,626 B2 | 3/2007 | Foley et al. | |
| 7,585,312 B2 | 9/2009 | Rawlins et al. | |
| 7,588,575 B2 | 9/2009 | Colleran et al. | |
| 7,641,674 B2 | 1/2010 | Young | |
| 7,744,629 B2* | 6/2010 | Hestad ................. | A61B 17/025 411/452 |
| 7,846,093 B2 | 12/2010 | Gorek et al. | |
| 7,862,593 B2 | 1/2011 | Clement et al. | |
| 7,931,673 B2 | 4/2011 | Hestad et al. | |
| 7,931,676 B2 | 4/2011 | Veldman et al. | |
| 7,947,064 B2 | 5/2011 | Bergeron et al. | |
| 8,016,866 B2 | 9/2011 | Warnick | |
| 9,289,250 B2* | 3/2016 | Wall ................... | A61B 17/7085 |
| 2004/0143265 A1 | 7/2004 | Landry et al. | |
| 2004/0260283 A1 | 12/2004 | Wu et al. | |
| 2005/0131408 A1* | 6/2005 | Sicvol et al. ..................... | 606/61 |

(Continued)

FOREIGN PATENT DOCUMENTS

| | | |
|---|---|---|
| EP | 2356944 A1 | 8/2011 |
| WO | 9830161 A1 | 7/1998 |
| WO | 2011084275 A1 | 7/2011 |

*Primary Examiner* — Ellen C Hammond
*Assistant Examiner* — Christina Negrellirodrigue

(57) ABSTRACT

A bone fastener includes a receiver defining a longitudinal axis and extending between a proximal end and a distal end, the proximal end including a first wall and a second wall that define an implant cavity, each wall having a proximal face. At least one of the first wall and the second wall include an extension extending proximally from the proximal face along the longitudinal axis, the extension having a distal end integral with the proximal face and a proximal end including a first locking part configured for fixation with a second locking part of an instrument. A bone penetrating member has a proximal end and a distal end, the proximal end of the bone penetrating member being connected with the distal end of the receiver.

17 Claims, 8 Drawing Sheets

(56) References Cited

U.S. PATENT DOCUMENTS

| | | |
|---|---|---|
| 2005/0171540 A1 | 8/2005 | Lim et al. |
| 2006/0079909 A1 | 4/2006 | Runco et al. |
| 2006/0229604 A1 | 10/2006 | Olsen et al. |
| 2007/0049931 A1 | 3/2007 | Justis et al. |
| 2007/0270815 A1 | 11/2007 | Johnson et al. |
| 2008/0082103 A1 | 4/2008 | Hutton et al. |
| 2008/0086131 A1 | 4/2008 | Daly et al. |
| 2008/0275456 A1* | 11/2008 | Vonwiller et al. ............... 606/99 |
| 2008/0294202 A1 | 11/2008 | Peterson et al. |
| 2009/0105759 A1 | 4/2009 | Gimbel et al. |
| 2010/0063552 A1 | 3/2010 | Chin et al. |
| 2010/0114179 A1* | 5/2010 | Moore ............... A61B 17/7032 606/308 |
| 2010/0152785 A1 | 6/2010 | Forton et al. |
| 2011/0004251 A1 | 1/2011 | Sweeney et al. |
| 2011/0077690 A1 | 3/2011 | Shin et al. |
| 2011/0098747 A1 | 4/2011 | Donner et al. |
| 2011/0178559 A1 | 7/2011 | Barry |
| 2011/0178560 A1* | 7/2011 | Butler ............... A61B 17/7086 606/86 A |
| 2011/0184415 A1 | 7/2011 | Anderson et al. |
| 2011/0202096 A1 | 8/2011 | White et al. |

* cited by examiner

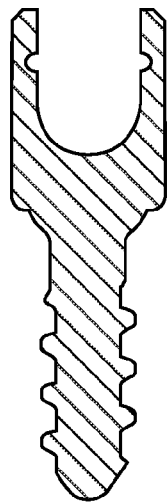
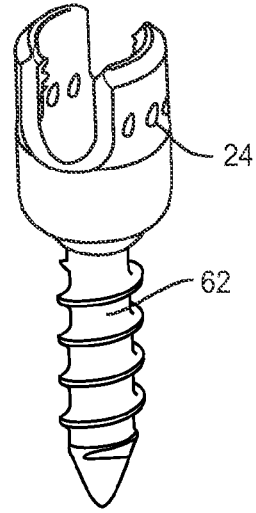
*FIG. 3A*  *FIG. 3B*
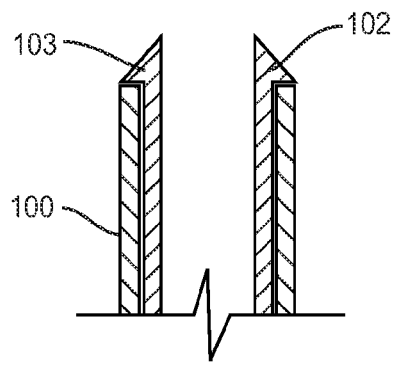
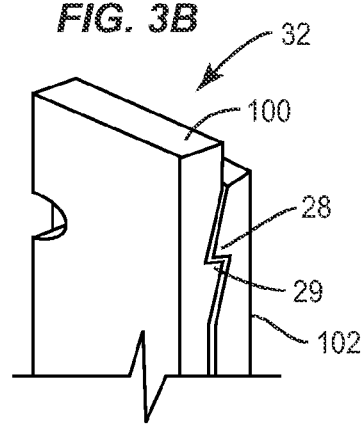
*FIG. 3C*  *FIG. 3D*
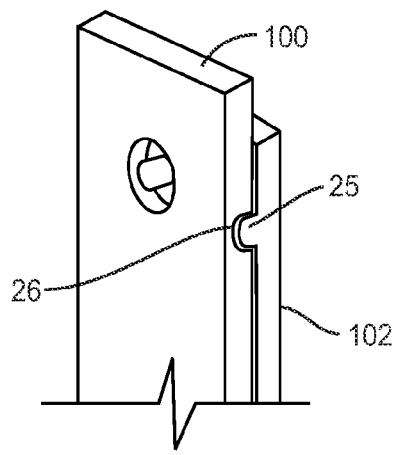
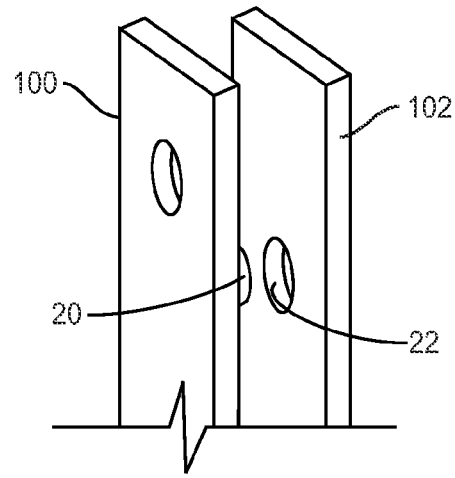
*FIG. 3E*  *FIG. 3F*

BONE FASTENER FOR A SPINAL SURGICAL SYSTEM

TECHNICAL FIELD

The present disclosure generally relates to medical devices and systems for the treatment of bone disorders, and more particularly to a spinal surgical system which includes a bone fastener and an extender configured to advance and guide components used in the treatment of bone disorders from outside the body to a location adjacent to a surgical site.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods may be attached via one or more bone fasteners to the exterior of two or more vertebral members. This disclosure describes an improvement over these prior art technologies.

SUMMARY OF THE INVENTION

Accordingly, a spinal surgery system is disclosed that includes a bone fastener and an extension configured to advance and guide components used in the treatment of bone disorders from outside the body to a location adjacent to a surgical site.

In one embodiment, in accordance with the principles of the present disclosure, a bone fastener is provided. The bone fastener includes a receiver defining a longitudinal axis and extending between a proximal end and a distal end, the proximal end including a first wall and a second wall that define an implant cavity. Each wall has a proximal face. At least one of the first wall and the second wall include an extension extending proximally from the proximal face along the longitudinal axis, the extension having a distal end integral with the proximal face and a proximal end including a first locking part configured for fixation with a second locking part of an instrument. A bone penetrating member has a proximal end and a distal end, the proximal end of the bone penetrating member being connected with the distal end of the receiver.

In one embodiment, a spinal surgical system is provided which includes a bone fastener having a receiver defining a longitudinal axis and extending between a proximal end and a distal end. The proximal end of the receiver includes a first arm and a second arm that define an implant cavity. Each arm has a proximal face. The first arm has a first extension integrally connected with the proximal face of the first arm along the longitudinal axis, the first extension having a locking part. The second arm has a second extension integrally connected with the proximal face of the second arm along the longitudinal axis, the second extension also having a locking part. The bone fastener has a bone penetrating member connected with the distal end of the receiver. The system also includes an instrument having a first elongated member and a second elongated member. The first elongated member includes an inner surface defining an elongated axial cavity configured for disposal of the first arm and a locking part configured for fixation with the locking part of the first arm. The second elongated member includes an inner surface defining an elongated axial cavity configured for disposal of the second arm and a locking part configured for fixation with the locking part of the second arm.

In another embodiment in accordance with the principles of the present disclosure, the system includes a bone fastener having a receiver defining a longitudinal axis and extending between a proximal end and a distal end. The proximal end of the receiver has a first arm and a second arm that define a U-shaped channel. Each arm has a proximal face. The first arm includes a first extension monolithically formed with the proximal face of the first arm along the longitudinal axis, the first extension having a protrusion. The second arm includes a second extension monolithically formed with the proximal face of the second arm along the longitudinal axis, the second extension having a protrusion. A bone penetrating member is connected with the distal end of the receiver. The system also includes an extender having a first elongated member and a second elongated member that define a rod cavity therebetween. The first elongated member includes an inner surface defining an elongated axial cavity configured for disposal of the first arm and an opening configured for fixation with the protrusion of the first arm. The second elongated member includes an inner surface defining an elongated axial cavity configured for disposal of the second arm and an opening configured for fixation with the protrusion of the second arm. The system also includes a vertebral rod configured for manipulation within the rod cavity and fixation within the U-shaped channel.

BRIEF DESCRIPTION OF THE DRAWINGS

The present disclosure will become more readily apparent from the specific description accompanied by the following drawings, in which:

FIG. 3A is a cross-sectional view of extender having a recess on the inside surface;

FIG. 3B is a cross-sectional view of extender having perforations on the extender;

FIG. 3C is a cross-sectional view of an alternative locking mechanism of the present invention;

FIG. 3D is a perspective view of an alternative locking mechanism of the present invention;

FIG. 3E is a perspective view of an alternative locking Mechanism of the present invention;

FIG. 3F is a perspective view of an alternative locking mechanism of the present invention;

Like reference numerals indicate similar parts throughout the figures.

DETAILED DESCRIPTION OF THE INVENTION

Figure 1:
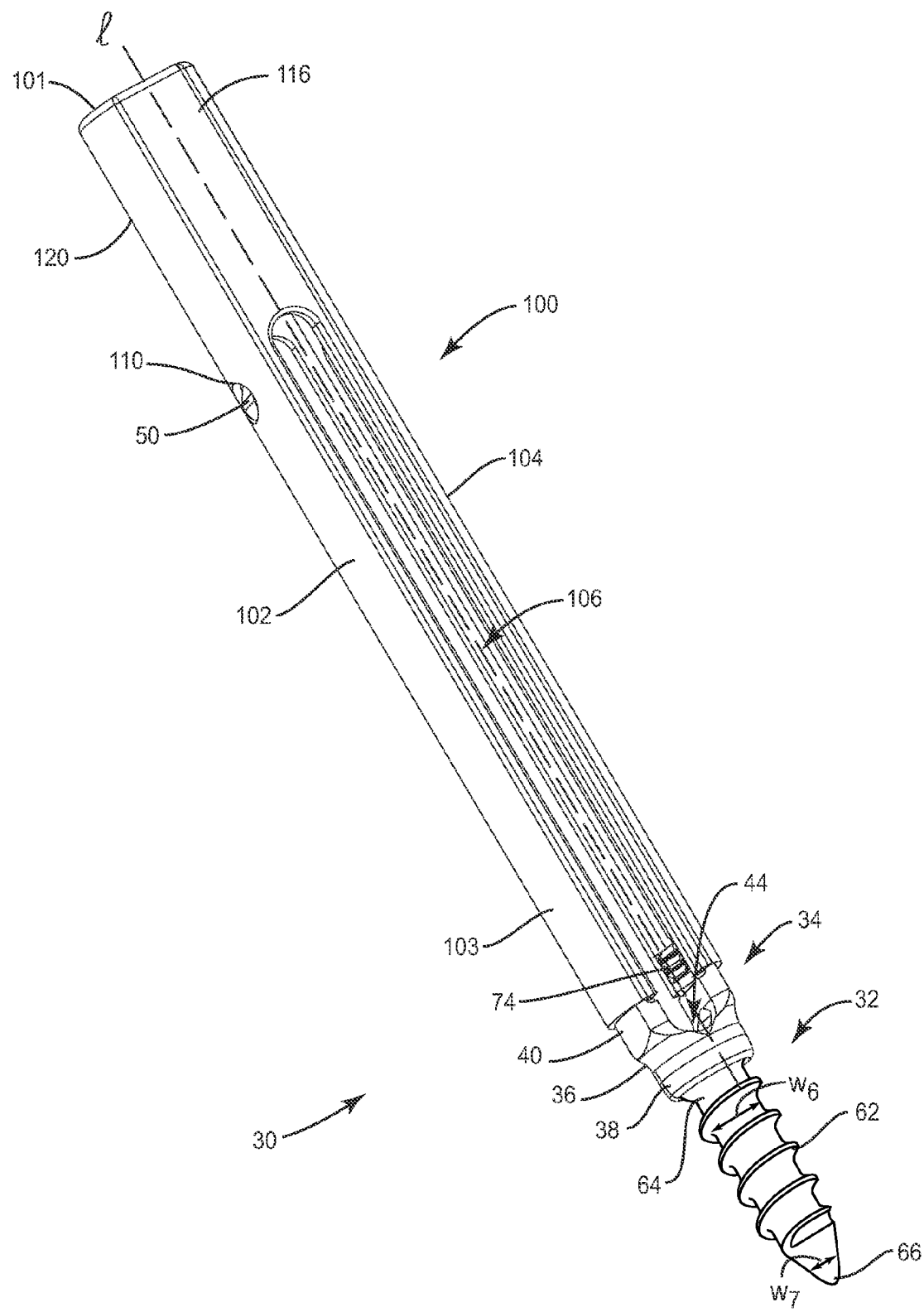
FIG. 1 is a perspective view of one embodiment of a bone fastener and one embodiment of an extender in accordance with the principles of the present disclosure.

The exemplary embodiments of the bone fastener and spinal surgical system disclosed are discussed in terms of medical devices for the treatment of bone disorders and more particularly, in terms of a spinal surgery system that includes a bone fastener and an extender configured to advance and guide components used in the treatment of bone disorders from outside the body to a location adjacent to a surgical site. It is contemplated that the disclosed spinal surgery system may be employed with minimally invasive systems and procedures which insert implants, instruments and other devices to perform operations through small skin incisions thereby allowing optimization of devices used in such procedures.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the present disclosure may be employed with surgical treatments including open surgery and minimally invasive procedures, of such disorders, such as, for example, discectomy, laminectomy, fusion, bone graft, implantable prosthetics and/or dynamic stabilization applications. It is contemplated that the present disclosure may be employed with other osteal and bone related applications, including those associated with diagnostics and therapeutics. It is further contemplated that the disclosed bone fastener may be employed in a surgical treatment with a patient in a prone or supine position, employing a posterior, lateral or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or approximately one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 2:
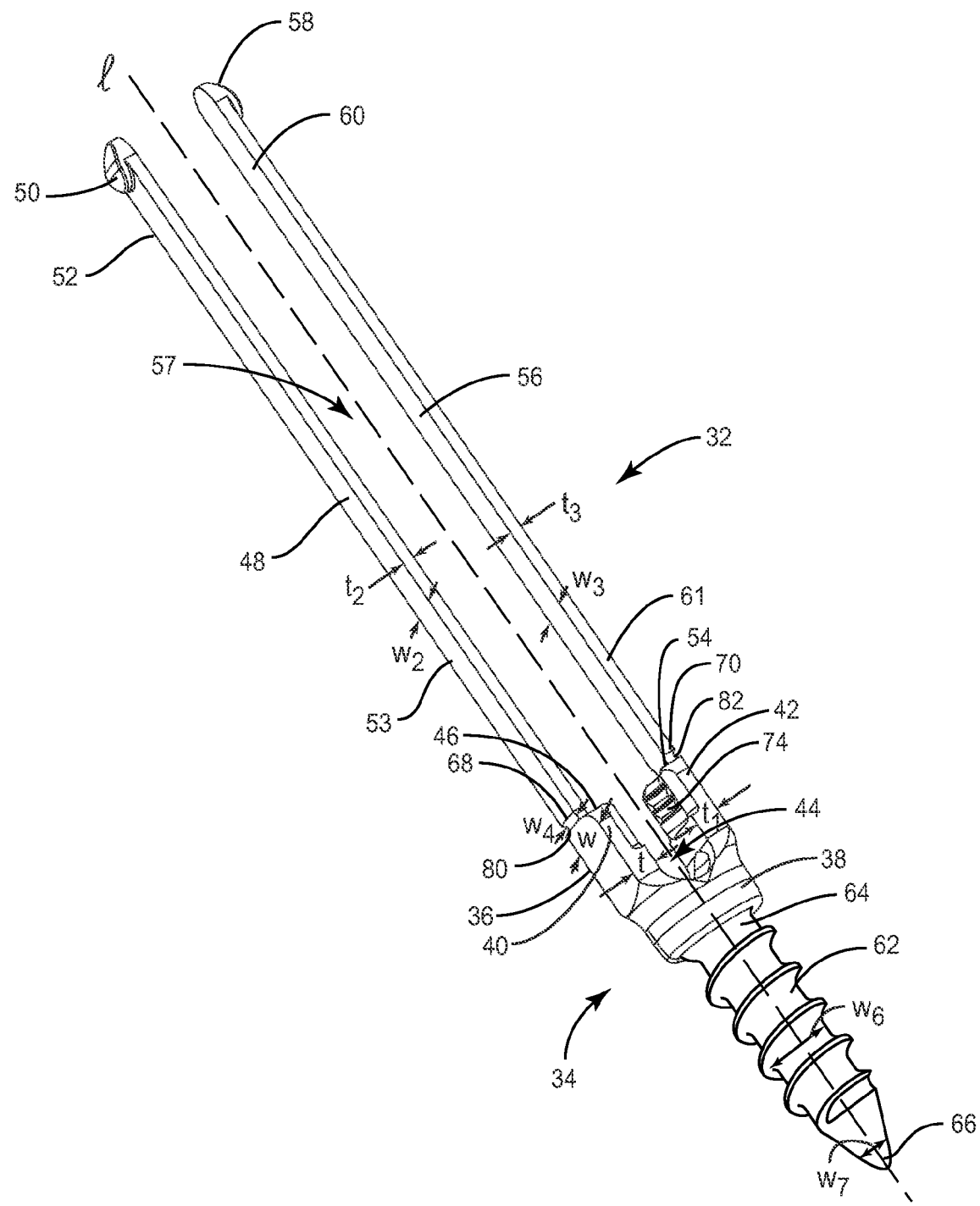
FIG. 2 is a perspective view of the bone fastener shown in FIG. 1.
Figure 3:
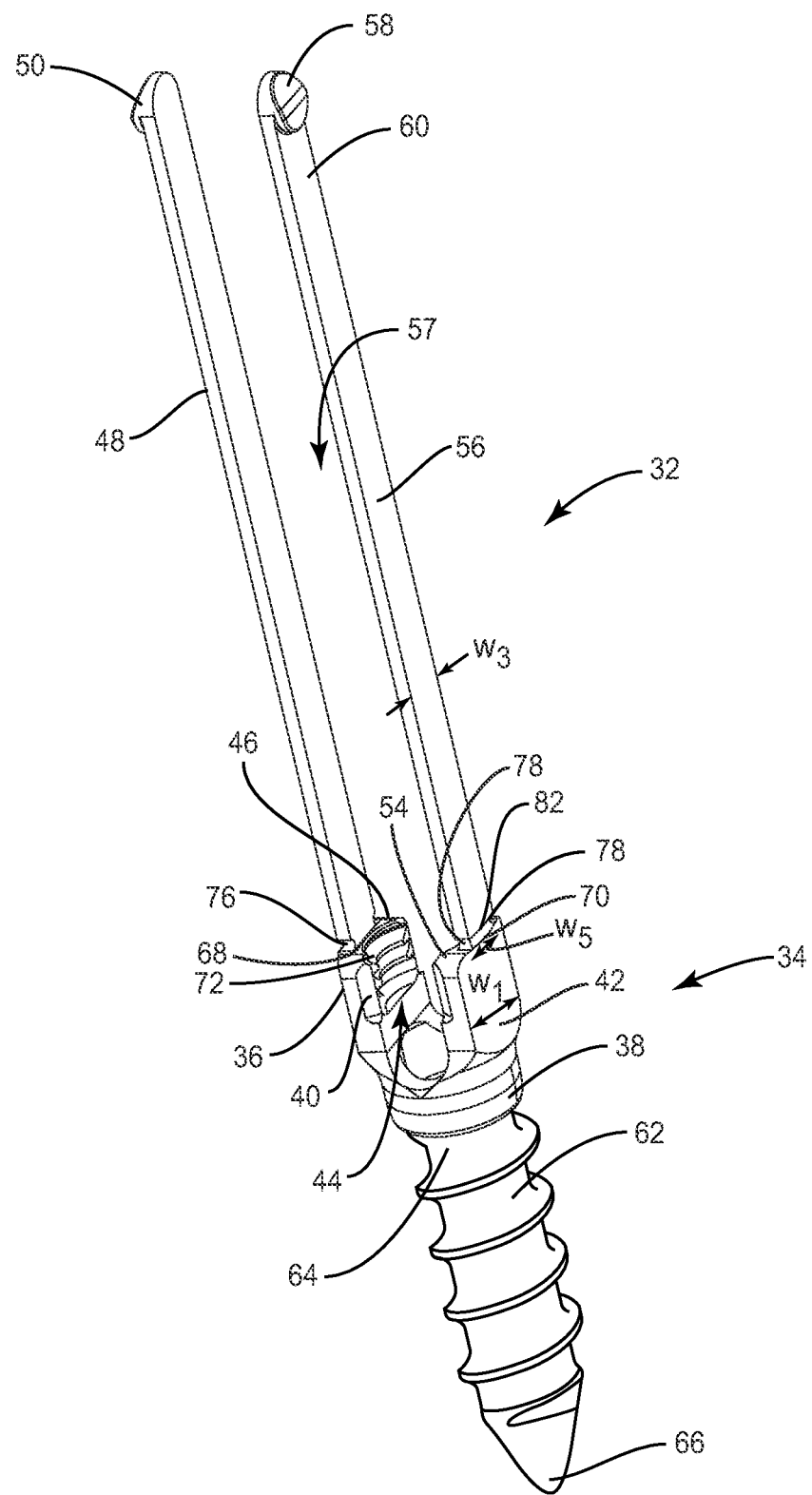
FIG. 3 is another perspective view of the bone fastener shown in FIG. 1.

The following discussion includes a description of a spinal surgery system that includes a bone fastener and an extender configured to advance and guide components used in the treatment of bone disorders from outside the body to a location adjacent to a surgical site. Related components and exemplary methods of employing the spinal surgery system in accordance with the principles of the present disclosure as well as alternate embodiments are also disclosed. Reference will now be made in detail to the exemplary embodiments of the present disclosure, which are illustrated in the accompanying figures. Turning now to FIGS. 1-3, there is illustrated components of a spinal surgical system 30 in accordance with the principles of the present disclosure.

The components of spinal surgical system 30 are fabricated from materials suitable for medical applications, including metals, polymers, ceramics, biocompatible materials and/or their composites, depending on the particular application and/or preference of a medical practitioner. For example, a bone fastener 32, and extender 100 and/or a vertebral rod, discussed below, of spinal surgical system 30 can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof such as calcium phosphate (e.g. SKELITE™ manufactured by Biologix Inc.), rigid polymers including polyphenylene, polyimide, polyimide, polyetherimide, polyethylene, polyurethanes of any durometer, epoxy and silicone. Different components of spinal surgical system 30 may have alternative material composites to achieve various desired characteristics such as strength, rigidity, elasticity, compliance, biomechanical performance, durability and radiolucency or imaging preference. The components of spinal surgical system 30 may also be fabricated from a heterogeneous material such as a combination of two or more of the above-described materials.

It is envisioned that the components of spinal surgical system 30 can be manufactured via various methods. For example, bone fastener 32 can be manufactured and assembled via injection-molding, insert-molding, overmolding, compression molding, transfer molding, co-extrusion, pultrusion, dip-coating, spray-coating, powder-coating, porous-coating, machining, milling from a solid stock material and their combinations. One skilled in the art, however, will realize that such materials and fabrication methods suitable for manufacture and assembly, in accordance with the present disclosure, would be appropriate.

Bone fastener 32, such as for example, a multi-axial of angled bone-fastener, fixed screw or spinal hook, is employed with spinal surgical system 30, which is configured for attachment to bone, such as, for example, one or more vertebrae during surgical treatment of a spinal disorder, examples of which are discussed herein. Bone fastener 32 includes a receiver 34 defining a longitudinal axis 1 and extending between a proximal end 36 and a distal end 38. Receiver 34 is configured to receive and couple a spinal construct, such as vertebral rod, for example, to bone fastener 32. Proximal end 36 includes a first wall, such as, for example, a first arm 40 and a second wall, such as, for example, a second arm 42 that define an implant cavity, such as, for example, a channel 44. In one embodiment, channel 44 has a generally U-shaped cross-section. However, it is envisioned that channel 44 may have other cross-sectional configurations, including, for example, V-shaped, polygonal or tapered.

First and second arms 40, 42 are disposed opposite one another and each have an arcuate shape. First arm 40 has a width w, a thickness t and includes a proximal face 46 and a first extension 48 monolithically formed with proximal face 46 of first extension 48. First extension 48 extends proximally from proximal face 46 along longitudinal axis 1 between proximal end 52 and distal end 53. Second arm 42 has a width $w_1$, a thickness $t_1$ and includes a proximal face 54 and a second extension 56 monolithically formed with proximal face 54 of second arm 42. Second extension 56 extends proximally from proximal face 54 along longitudinal axis 1 between a proximal end 60 and a distal end 61. It is envisioned that first and second extensions 48, 56 may be removably attached with proximal faces 46, 54 such that at least a portion of first and second extensions 48, 56 may be separated from receiver 34. For example, first and second extensions 48, 56 may be clipped to proximal faces 46, 54 of receiver 34 via clips positioned at distal ends 53, 61 of first and second extensions 48, 56. Alternatively, distal ends 53, 61 of first and second extensions 48, 56 may be positioned in corresponding recesses in proximal faces 46, 54 of first and second arms 40, 42 so as to be held in place. In an alternative embodiment, proximal face 46 does not exist and is in accordance with the principles of the present invention is shown in FIG. 3B. In FIG. 3B, perforations 24 are located at the bone penetrating member and can act as a break-off region for the device. It is envisioned that there can be one row of perforations including one or a plurality of perforations or multiple rows.

First and second extensions 48, 56 are substantially similar to one another, and are sized and shaped to extend from proximal faces 46, 54 of first and second arms 40, 42. First extension 48 and/or second extension 56 has/have a substantially uniformly continuous even surface configuration. That is, first extension 48 and/or second extension 56 has/have smooth surfaces that are not interrupted by any gaps or protrusions. In one embodiment, first and second extensions 48, 56 have inner surfaces and outer surfaces that are planar. However, it is envisioned that first and second extensions 48, 56 may have an arcuate surface configuration such that inner surfaces and/or outer surfaces of first and second extensions 48, 56 correspond to the arcuate shape of first and second walls 40, 42 from which first and second extensions 48, 56 extend. That is, the inner surfaces of first and second extensions 48, 56 can be concavely curved, while the outer surfaces thereof are convexly curved. Other configurations in this respect are also envisioned by the present disclosure and fall within the spirit of the present invention.

First extension 48 has a width $w_2$ that is less than width w of first arm 40, as shown in FIG. 2, and second extension 56 has a width $w_3$ that is less than width $w_1$ of second arm 42, as shown in FIG. 3. In accordance with the principles of the present disclosure, it is envisioned that first and second extensions 48, 56 may have a width that is approximately equal to widths w and $w_1$ of first and second arms 40, 42. First extension 48 has a thickness $t_2$ that is less than thickness t of first arm 40, and second extension 56 has a thickness $t_3$ that is less than thickness $t_1$ of second arm 42. Similarly it is also envisioned that first and second extensions 48, 56 may have a thickness that is approximately equal to thicknesses t and $t_1$ of first and second arms 40, 42.

First and second extensions 48, 56 are substantially parallel to one another and have a length that allows proximal ends 52, 60 to be positioned outside a patient's body, while distal ends 53, 61 are coupled to proximal faces 46, 54 of receiver 34 when bone fastener 32 is fully implanted in a vertebra and receiver 34 is positioned adjacent to the vertebrae. In the alternative, first and second extensions 48, 56 are substantially parallel to one another and have a length that allows proximal ends 52, 60 to be within a retractor and accessible, but not outside the body, when used in a mini-open surgical procedure. First and second extensions 48, 56 define a slot 57 which is aligned with channel 44 in receiver 34 such that slot 57 and channel 44 are continuous to allow a vertebral construct, such as, for example, a vertebral rod, to move within slot 57 and into channel 44.

First extension 48 includes a first locking part, such as, for example, a protrusion 50 at proximal end 52 thereof, and second extension 56 includes a first locking part, such as, for example, a protrusion 58 at proximal end 60 thereof. Protrusions 50, 58 are disposed on the outer surfaces of first and second extensions 48, 56 and are configured for fixation with a second locking part of an instrument, such as, for example, extender 100 so as to fix bone fastener 32 in position and limit relative motion between bone fastener 32 and extender 100, as will be described. In an alternative embodiment, a protrusion can be positioned on the inner diameter of the outer body and the screw extension can be equipped with a cavity configured to mate with the protrusion on the outer body. This arrangement fixes bone fastener 32 in position and limits relative motion between bone fastener 32 and extender 100.

In one embodiment, protrusions 50, 58 have a shape that is round or oval. However, it is envisioned that protrusions 50, 58 can be variously configured with regard to size and shape, and the shape may be selected from the group consisting of rectangular, triangular, polygonal and hexagonal, for example. It is also envisioned that first and second arms 40, 42 may include alternate locking or fastening parts to fix bone fastener 32 with extender 100 such as, integral connection, threaded engagement, clips, friction fit, interference fit, pins and/or adhesive.

Bone fastener 32 includes an integral connection 68 extending between first extension 48 and proximal face 46 of first arm 40, as shown in FIG. 2, and an integral connection 70 extending between second extension 56 and proximal face 54 of second arm 42, as shown in FIG. 3. In one embodiment, integral connections 68, 70 are disposed at distal ends 53, 61 of first and second extensions 48, 56, where second extensions 48, 56 meet proximal faces 46, 54 of first and second arms 40, 42. It is also envisioned that integral connections 68, 70 may be disposed at any portion along the length of first and second extensions 48, 56. Integral connection 68 has a width $w_4$ that is less than width of first extension 48 and integral connection 70 has a width $w_5$ that is less than width $w_3$ of second extension 56. The reduced widths of integral connections 68, 70 are due to reliefs 80, 82 (best seen in FIGS. 2 and 3) that are disposed in the outer surfaces thereof which form a recess extending perpendicularly relative to longitudinal axis l. In one embodiment, the integral connection is a portion of the extension that has a reduced cross-sectional area when compared to the rest of the extension. This reduced area, either due to perforations, notches, recesses or other configurations, allows a break-off section of the extensions. In another embodiment, reliefs 80, 82 have arcuate cross-sectional configurations. However, it is envisioned that the reliefs 80, 82 may have other cross-sectional configurations, including, for example, triangular, polygonal or tapered.

Integral connection 68 has a thickness that is less than thickness $t_2$ of first extension 48 and integral connection 70 has a thickness that is less than thickness $t_3$ of second extension 56. However, it is envisioned that widths $w_4$, $w_5$ of integral connections 68, 70 may be approximately equal to widths $w_2$, $w_3$ of first and second extensions 48, 56. It is also envisioned that the thicknesses of integral connections 68, 70 may be approximately equal to thicknesses $t_2$ and $t_3$ of first and second extensions 68, 70. The recess, notches or groves can also be located on the inside of the extension as shown in FIG. 3A. The reduced thicknesses of integral connections 68, 70 is due to notches 76, 78 extending into the side surfaces thereof. In one embodiment, notches 76, 78 have arcuate cross-sectional configurations. However, it is envisioned that notches 76, 78 may have other cross-sectional configurations, including, for example, triangular, polygonal or tapered. It is this reduction in the cross-sectional area due to the recesses, notches or perforations that provide for the break-off mechanism of the extensions.

The inner surfaces of first and second extensions 48, 56 are continuous with the inner surfaces of integral connections 68, 70 such that there are no gaps therebetween. It is envisioned that integral connections 68, 70 may be formed from a material which is different from the material used to form receiver 34 and/or first and second extensions 48, 56 such that integral connections 68, 70 break off from the receiver 34 when a force is applied thereto thereby allowing at least a portion of first and second extensions 48, 56 to be separated from receiver 34. It is envisioned that these notches can have different forms, shapes and depths into the side surfaces so as to provide different break-of profiles of the extensions 48, 56 from the receiver 34. That is, different forms, shapes and depths of the notches into the side surfaces of the extensions will require different amounts of force to break-off the extensions 48, 56 from receiver 34.

Bone fastener 32 further includes a bone-penetrating member 62, such as a multi-axial screw, fixed screw or spinal hook, that extends between a proximal end 64 and a distal end 66 and is configured to connect with distal end 38 of receiver 34. Bone penetrating member 62 is configured for fixation within vertebrae and has a cylindrical shaft configuration. In one embodiment of the present disclosure, bone penetrating member 62 tapers from a first width $w_6$ at proximal end 64 to a second, reduced width w; at distal end 66. Receiver 34 has a bore in distal end 38 configured to receive proximal end 64 of bone penetrating member 62 to couple bone penetrating member 62 to receiver 34. As such, the bore in distal end 38 of receiver 34 has a diameter which is greater than width $w_6$ in proximal end 64 of bone penetrating member 62 such that proximal end 64 of bone penetrating member 62 is seated within the bore in proximal end 36 of receiver 34. Bone penetrating member 62 is longitudinally aligned with receiver 34 along longitudinal axis l. In one embodiment, bone penetrating member 62 is rotationally fixed to receiver 34 so as to rotate around one or more axis. That is, bone penetrating member 62 is pivotable to a plurality of axial orientations relative to receiver 34. It is contemplated that bone penetrating member 62 or portions thereof can have various dimensions, for example, with regard to length, width, diameter and thickness. It is further contemplated that the cross-sectional geometry may have various configurations including, for example, round, oval, rectangular, irregular, consistent, variable, uniform and non-uniform.

As shown in FIGS. 1 and 4-6, spinal surgical system 30 further includes extender 100 extending between a proximal end 101 and a distal end 103 opposite proximal end 101. Extender 100 includes upper and lower surfaces 116, 118 extending between side surfaces 120, 122. In one embodiment, upper and lower surfaces 116, 118 are planar and side surfaces 120, 122 are both convexly curved. However, it is envisioned that upper and lower surfaces 116, 118 and side surfaces 120, 122 may all be convexly curved, such that extender 100 has a cylindrical cross-section. Alternatively, upper and lower surfaces 116, 118 and side surfaces 120, 122 may be planar, such that extender 100 has a rectangular or square cross-section. It is contemplated that the cross-sectional geometry of extender 100 may have various configurations including, for example, round, oval, polygonal, irregular, consistent, variable, uniform and non-uniform.

Extender 100 includes a first elongated member 102 and a second elongated member 104 that define a rod cavity 106 therebetween. In one embodiment, first and second elongated members 102, 104 are integrally connected to one another. However, it is envisioned that first and second elongated members 102, 104 may be separate from one another and are connected via clips, a friction fit, an interference fit, pins and/or an adhesive. Rod cavity 106 may be used to facilitate positioning of a spinal construct, such as a vertebral rod, relative to bone fastener 32. Rod cavity 106 extends longitudinally to distal end 103 and through upper and lower surfaces 116, 118 of extender 100 terminating prior to proximal end 101. That is, rod cavity 106 forms an opening through distal end 103 and upper and lower surfaces 116, 118, but does not extend through proximal end 101. First and second elongated members 102, 104 are coupled to one another at distal end 101. Rod cavity 106 terminates at the point where the first and second elongated members 102, 104 couple. Rod cavity 106 is configured so that a vertebral construct, such as vertebral rod, and/or an instrument can pass down the cavity.

In one embodiment, rod cavity 106 has a length such that rod cavity 106 is accessible outside the body of a patient when bone fastener 32 is fully implanted in a vertebra. However, it is envisioned that the length and width of rod cavity 106 may be varied depending upon, for example, the particular methods, instruments and/or vertebral constructs being employed. Rod cavity 106, slot 57 between first and second extensions 48, 56 and channel 44 between first and second arms 40, 42 are continuous and define a pathway from an incision in the skin of a patient to a location adjacent a surgical site for the delivery of implants, instruments, and/or other devices.

First elongated member 102 includes an inner surface defining an elongated axial cavity 108 configured for disposal of first arm 40 and a cavity defining a second locking part, such as, for example, an opening 110 configured for fixation with protrusion 50 of first extension 48. Second elongated member 104 includes an inner surface defining an elongated axial cavity 112 configured for disposal of second arm 42 and a cavity defining a second locking part, such as, for example, an opening 114, configured for fixation with protrusion 58 of second extension 56. Openings 110, 114 are configured to receive protrusions 50, 58 of bone fastener 32. In one embodiment, openings 110, 114 are oval or round. However, it is envisioned that openings 110, 114 can be variously configured with regard to size and shape, and may have a shape which is rectangular, triangular, hexagonal, or any other shape that corresponds to the shape of protrusions 50, 58 such that protrusions 50, 58 may be received within openings 110, 114. Openings 110, 114 may extend through side surfaces 120, 122. However, it is envisioned that openings 110, 114 may extend through upper and lower surfaces 116, 118. Alternatively, openings 110, 114 may extend into side surfaces 120, 122 without extending through the same such that protrusions 50, 58 do not extend through extender 100 when protrusions 50, 58 are received within openings 110, 114.

Extender 100 is disposed about at least a portion of bone fastener 32 such that extender 100 is coaxially disposed about bone fastener 32. In particular, first and second extensions 48, 56 of bone fastener 32 are inserted into distal end 103 of extender 100, leading with proximal ends 52, 60 of first and second extensions 48, 56. Bone fastener 32 is advanced longitudinally through extender 100 toward proximal end 101 of extender 100 with first and second extensions 48, 56 of bone fastener 32 parallel to side surfaces 120, 122 of extender 100. Bone fastener 32 is advanced until protrusions 50, 58 of first and second extensions 48, 56 are received within openings 110, 114, which connects bone fastener 32 with extender 100. Protrusions 50, 58 are sized and configured to be received within openings 110, 114 such that protrusions 50, 58 occupy a significant portion of openings 110, 114 to prevent movement of bone fastener 32 relative to extender 100 when protrusions 50, 58 are received within openings 110, 114.

Figure 2A:
FIG. 2A is a perspective view of the bone fastener.
Figure 2B:
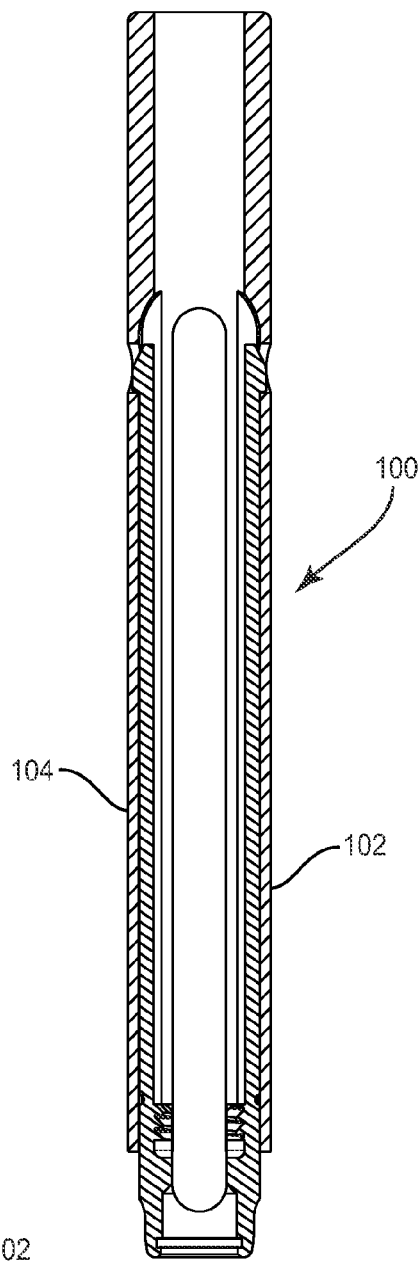
FIG. 2B is a cross-sectional view of the bone fastener with the extenders.
Figure 2C:
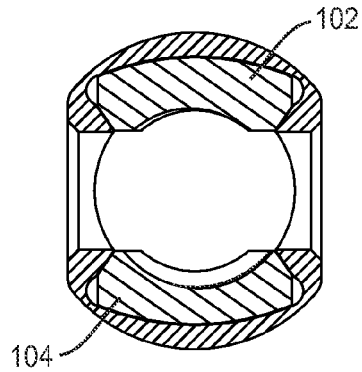
FIG. 2C is a cross-sectional view of the extender and receiver.

First and second elongated members 102, 104 of extender 100 include distal faces 124, 126 at distal end 103 of extender 100 that are configured to engage at least a portion of proximal faces 46, 54 of bone fastener 32 to further prevent movement of bone fastener 32 relative to extender 100. Accordingly, extender 100 has a length such that distal faces 124, 126 engage at least a portion of proximal faces 46, 54 when protrusions 50, 58 of first and second extensions 48, 56 are received within openings 110, 114. That is, bone fastener 32 is advanced until protrusions 50, 58 of first and second extensions 48, 56 are received within openings 110, 114 and distal faces 124, 126 engage at least a portion of proximal faces 46, 54, which connects bone fastener 32 with extender 100. In this configuration, bone fastener 32 is restricted from moving relative to extender 100. It is envisioned that distal faces 124, 126 and proximal faces 46, 54 are planar, however other mating configurations are possible. It is also envisioned that the elongated members of the extender extend past proximal faces 46 and 54 so that the extender shields the integral connection from stress while the extender is attached. That is, since the extender is used to manipulate the receiver, this shielding effect is important so as not to transmit the manipulation forces so as to accidentally break-off the extensions. This is shown in FIGS. 2A-2C. In one embodiment, shown in FIGS. 2B-2C, the end of the elongated members slightly wrap around the arms of the receiver. This not only makes the assembly more rigid but also helps to shield the integral connection from stress.

In one embodiment, surgical system 30 includes a vertebral rod configured for manipulation within rod cavity 106 of extender 100 and fixation within channel 44 between first and second arms 40, 42. It is also envisioned that the vertebral rod may have a size and shape that corresponds to the size and shape of rod cavity 106 and slot 57 between first and second extensions 48, 56 such that the vertebral rod may be moved along the length of rod cavity 106 and/or slot 57 and into channel 44.

In one embodiment, channel 44 of receiver 34 is defined by an inner surface of first and second arms 40, 42 and includes internal threads 72, 74 formed on the inner surface of first and second arms 40, 42. Internal threads 72, 74 may be configured to receive a set screw to fix the position of a vertebral rod within channel 44 of receiver 34. It is envisioned that internal threads 72, 74 may be reverse angle threads. That is, threads 72, 74 may include a forward face that points down and in toward receiver 34, as disclosed in commonly owned U.S. Pat. No. 6,296,642, the disclosure of which is incorporated herein by reference. In one embodiment, the inner surfaces of first and second extensions 48, 56 include internal threads which are continuous with internal threads 72, 74 formed on the inner surface of first and second arms 40, 42. In addition to defining a pathway for implants/instruments, the proximal end can also include features that allow for the attachment of other instruments. This feature allows the extender to become part of a larger instrument system used in spinal and other surgical procedures.

Figure 4:
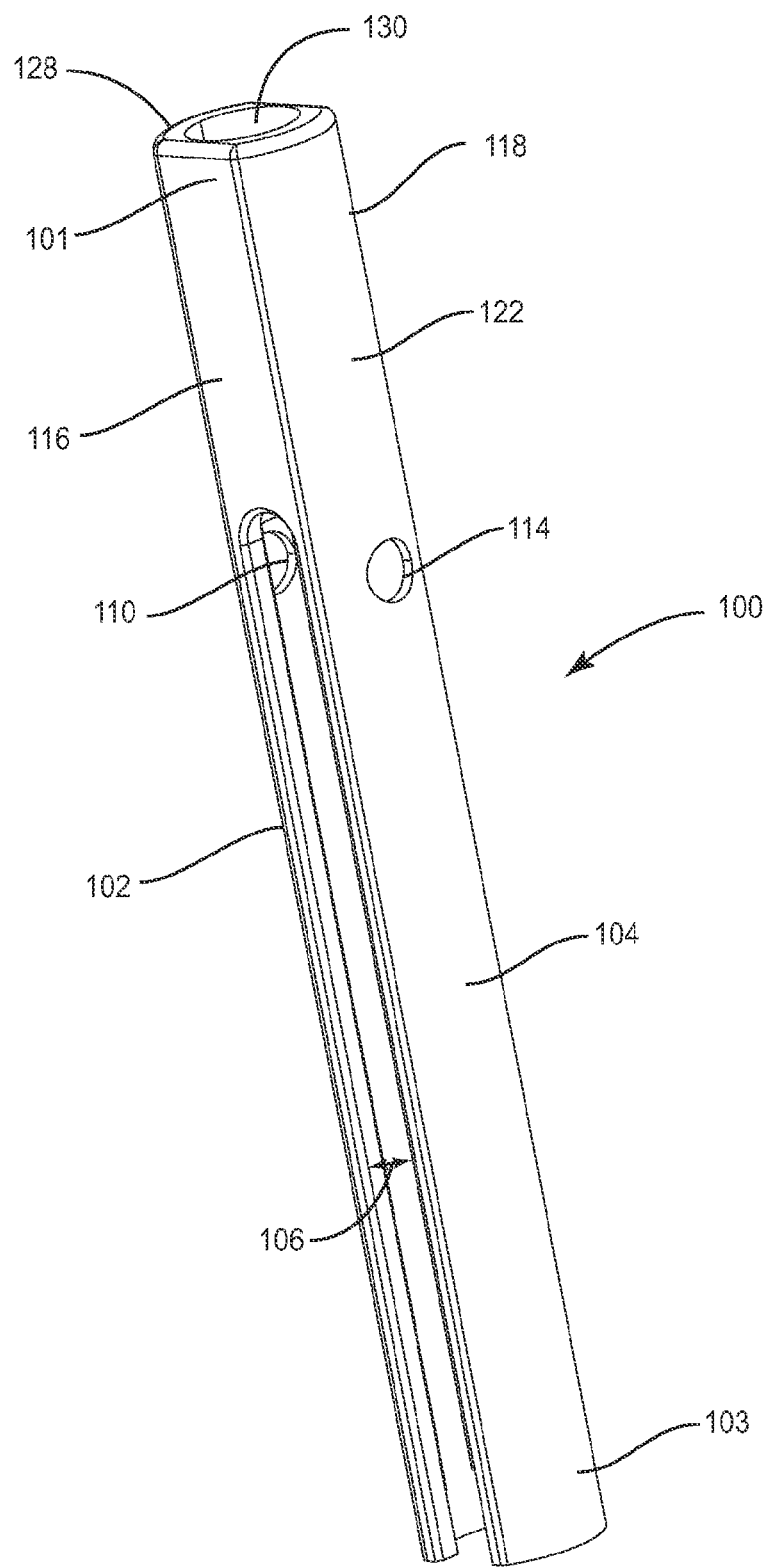
FIG. 4 is a perspective view of the extender shown in FIG. 1.
Figure 5:
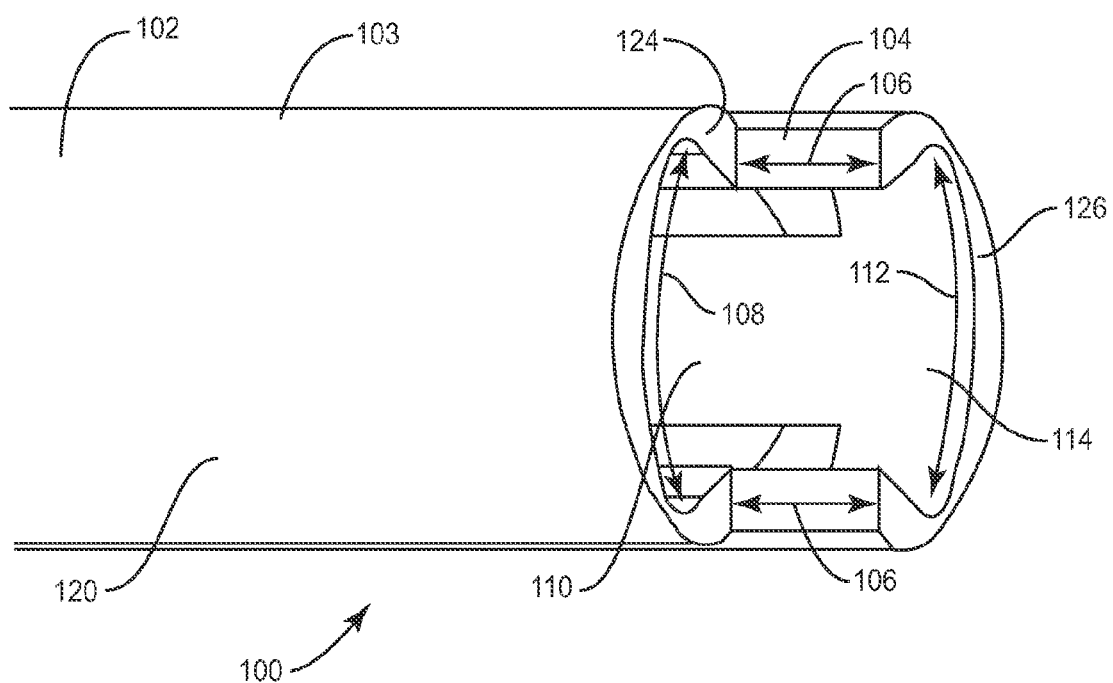
FIG. 5 is a perspective view of a distal end of the extender shown in FIG. 1.
Figure 6:
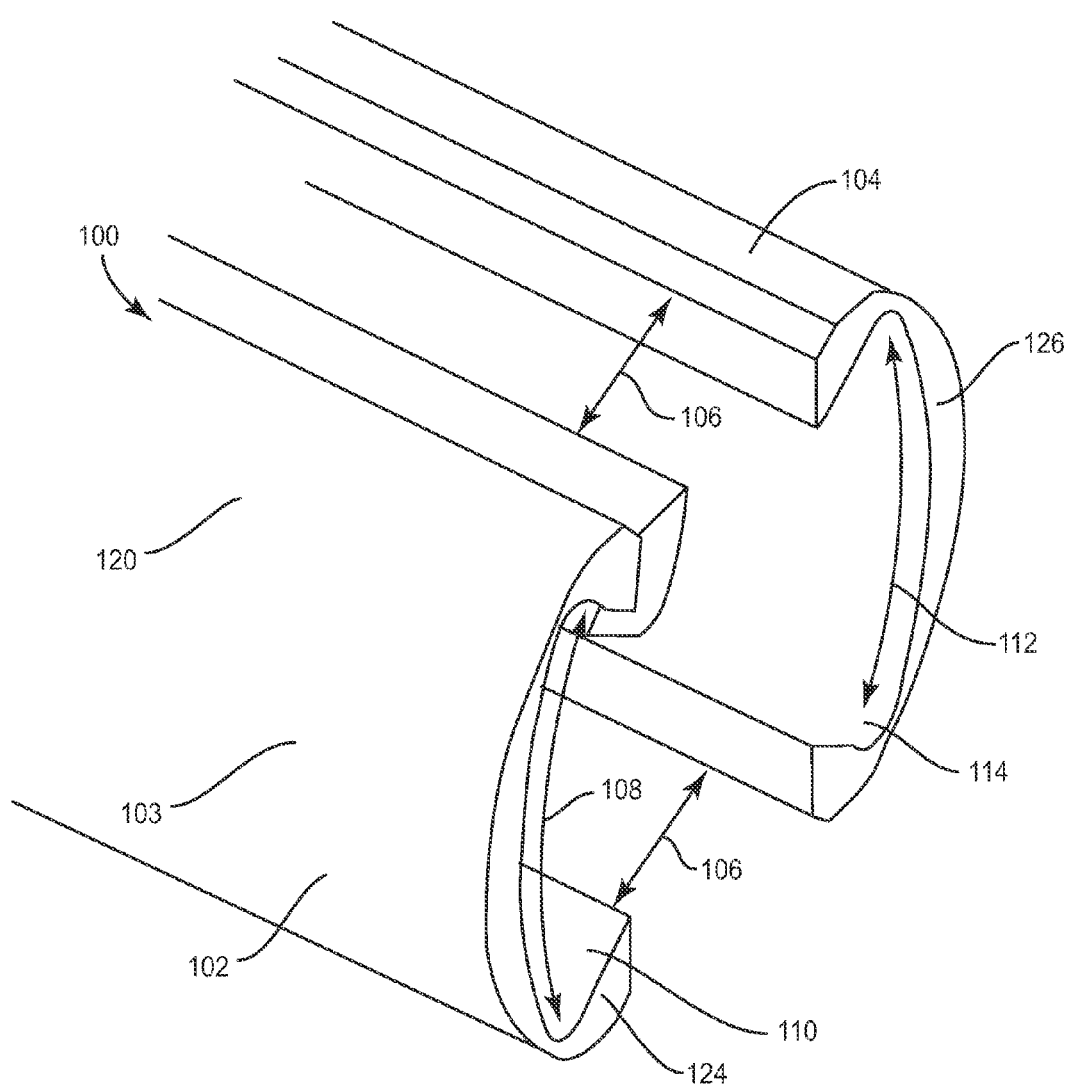
FIG. 6 is a perspective, close-up view of the distal end of the extender shown in FIG. 5.

In one embodiment, best shown in FIG. 4, proximal end 101 of extender 100 includes a proximal face 128 having a recessed portion 130 formed therein sized and shaped to provide access for tools and/or bone attachment components. Recessed portion 130 is continuous with rod cavity 106 of extender 100, slot 57 between first and second extensions 48, 56 and channel 44 between first and second arms 40, 42 of bone fastener 32 such that sections 130, 106, 57 and 44 define a pathway from an incision in the skin of a patient to a location adjacent a surgical site for the delivery of plants, instruments and/or other devices.

In assembly, operation and use, spinal surgical system 30 is employed with a surgical procedure for treatment of a spinal disorder affecting a section of a spine of a patient, as discussed herein. For example, spinal surgical system 30 can be used with a surgical procedure for treatment of a condition or injury of an affected section of the spine including vertebrae. It is contemplated that spinal surgical system 30, including a rod, is attached to vertebrae to facilitate fusion and/or dynamic stabilization applications of the affected section of the spine as a therapeutic treatment, while providing flexion, extension and/or torsion capability.

In use, to treat the affected section of the spine, a medical practitioner obtains access to a surgical site including a vertebra in any appropriate manner, such as through incision and retraction of tissues. It is envisioned that spinal surgical system 30 may be used in any existing surgical method or technique including open surgery, mini-open surgery, minimally invasive surgery and percutaneous surgical implantation, whereby vertebrae is accessed through a micro-incision or sleeve that provides a protected passageway to the area. Once access to the surgical site is obtained, the particular surgical procedure is performed for treating the spinal disorder. Spinal surgical system 30 is then employed to augment the surgical treatment. Spinal surgical system 30 can be delivered or implanted as a pre-assembled device or can be assembled in situ. Spinal surgical system 30 may be completely or partially revised, removed or replaced, for example, removing instrument 100, a vertebral rod and/or one or all of the components of bone fastener 32 during or after the surgical procedure.

Bone fastener 32 may be employed as a bone screw, pedicle screw or multi-axial screw used in spinal surgery. It is contemplated that bone fastener 32 may be coated with an osteoconductive material such as hydroxyapatite and/or osteoinductive agent such as a bone morphogenic protein for enhanced bony fixation. Bone fastener 32 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used.

It will be understood that various modifications may be made to the embodiments disclosed herein. Therefore, the above description should not be construed as limiting, but merely as exemplifications of the various embodiments. Those skilled in the art will envision other modifications within the scope and spirit of the claims appended hereto.

Alternate locking mechanisms in accordance with the principles of the present invention are shown in FIGS. 3C-3F. In FIG. 3C it is shown that the extension protrudes past the proximal end of the extender in order to lock the extenders into place. In FIG. 3D, a ratchet 29 and tooth 28 configuration is provided as a locking mechanism in replace of the protrusion and recess discussed herein. In FIG. 3E, one side of a ridge 25 and groove 26 locking mechanism is shown. In this embodiment, access to the locking mechanism port 27 is provided on the outside surface so as to provide access to the locking mechanism to allow release of the extender from the elongated member 103. In FIG. 3F, a protrusion 20 is located on the extender 100 and a hole 22 that mates with the protrusion 20 is located on the extension elongated member 103. In this embodiment, the hole 22 can be offset to as to provide access to release the locking mechanism. Although only one side is shown it is envisioned that this arrangement can be located on both sides of the bone fastener. These figures show alternate locking mechanisms that can be used in practicing the bone fastener of the present disclosure and it is envisioned that other configurations can be used as a locking mechanism without deviating from the principles of the present disclosure.

What is claimed is:

1. A spinal surgical system comprising:
   a bone fastener comprising:
   a receiver defining a longitudinal axis and extending between a proximal end and a distal end, the proximal end including a first wall and a second wall that define an implant cavity, each wall including a proximal face,
   at least one of the first wall and the second wall comprising an extension extending proximally from the proximal face along the longitudinal axis, the extension including a distal end monolithically formed with the proximal face and a proximal end comprising a protrusion defining a first locking part, the first locking part being fixed relative to an outer surface of the extension, and
   a bone penetrating member having a proximal end and a distal end, the proximal end of the bone penetrating member connected with the distal end of the receiver,
   wherein the first and second walls each include an inner surface that defines the implant cavity, the inner surfaces including threads adjacent the proximal faces thereof; and
   an instrument including first and second elongated members, at least one of the elongated members including an inner surface defining an elongated axial cavity configured for disposal of the extension and a cavity defining a second locking part configured for disposal of the protrusion.

2. The system of claim 1, wherein the extension is configured so as to extend past the proximal face so that the extension shields an integral connection defined by the extension and the first and second walls from stress while the extension is attached.

3. The system of claim 1, wherein the extension includes an arcuate surface configuration.

4. The system of claim 1, wherein the extension and the first and second walls define an integral connection therebetween, the integral connection includes a relief.

5. The system of claim 1, wherein the extension and the first and second walls define an integral connection therebetween, the integral connection includes a reduced thickness portion or perforations.

6. The system of claim 1, further comprising the first wall comprising a first extension extending proximally from the proximal face of the first wall and the second wall comprising a second extension extending proximally from the proximal face of the second wall.

7. The system of claim 1, wherein the instrument includes an extender.

8. The system of claim 1, wherein the instrument includes an extender such that the first elongated member and the second elongated member define a cavity therebetween for disposal of a vertebral rod.

9. The system of claim 1, wherein the protrusion has an arcuate configuration.

10. The bone fastener of claim 1, wherein the locking part being protrusion is removably disposed in the cavity to fix the bone fastener with the instrument.

11. A spinal surgical system comprising:
    a bone fastener comprising a receiver defining a longitudinal axis and extending between a proximal end and a distal end, the proximal end including a first arm and a second arm that define an implant cavity, each arm including a proximal face, the first arm comprising a first extension monolithically formed with the proximal face of the first arm along the longitudinal axis, the first extension comprising a protrusion defining a locking part that is fixed relative to an outer surface of the first extension, the second arm comprising a second extension monolithically formed with the proximal face of the second arm along the longitudinal axis, the second extension comprising a protrusion defining a locking part that is fixed relative to an outer surface of the second extension, the bone fastener further comprising a bone penetrating member connected with the distal end of the receiver; and
    an instrument including a first elongated member and a second elongated member, the first elongated member includes an inner surface defining an elongated axial cavity configured for disposal of the first arm and a locking part configured for fixation with the locking part of the first arm, the second elongated member includes an inner surface defining an elongated axial cavity configured for disposal of the second arm and a locking part configured for fixation with the locking part of the second arm.

12. The system of claim 11, wherein the first and second extensions are configured so as to wrap around the first and second arms so that lateral forces placed on the first and second extensions are transmitted to a head of the bone penetrating member.

13. The system of claim 11, wherein the extensions and the arms define an integral connection therebetween, wherein the integral connections include a relief.

14. The system of claim 11, wherein the extensions and the arms define an integral connection therebetween, respectively, the integral connections including a reduced thickness portion.

15. The system of claim 11, wherein the locking part of the first arm and the locking part of the first elongated member comprise a cavity and a protrusion configured for disposal in the cavity.

16. The system of claim 11, wherein the locking part of the first arm and the locking part of the first elongated member comprise a cavity and a protrusion configured for disposal in the cavity, and the locking part of the second arm and the locking part of the second elongated member comprise a cavity and a protrusion configured for disposal in the cavity.

17. A spinal surgical system comprising:
    a bone fastener comprising a receiver defining a longitudinal axis and extending between a proximal end and a distal end, the proximal end including a first arm and a second arm that define a U-shaped channel, each arm including a proximal face, the first arm comprising a first extension monolithically formed with the proximal face of the first arm along the longitudinal axis, the first extension comprising a protrusion that is fixed relative to an outer surface of the first extension, the second arm comprising a second extension monolithically formed with the proximal face of the second arm along the longitudinal axis, the second extension comprising a protrusion that is fixed relative to an outer surface of the second extension, the bone fastener further comprising a bone penetrating member connected with the distal end of the receiver;

an extender including a first elongated member and a second elongated member that define a rod cavity therebetween, the first elongated member includes an inner surface defining an elongated axial cavity configured for disposal of the first arm and an opening configured for fixation with the protrusion of the first arm, the second elongated member includes an inner surface defining an elongated axial cavity configured for disposal of the second arm and an opening configured for fixation with the protrusion of the second arm; and a vertebral rod configured for manipulation within the rod cavity and fixation within the U-shaped channel.

* * * * *